(12) United States Patent
Falco et al.

(10) Patent No.: US 7,729,744 B2
(45) Date of Patent: Jun. 1, 2010

(54) VERIFYING LESION CHARACTERISTICS USING BEAM SHAPES

(75) Inventors: Tony Falco, Montreal (CA); François Perraton, Montreal (CA)

(73) Assignee: Resonant Medical, Inc., Montreal, Quebec (CA)

( * ) Notice: Subject to any disclaimer, the term of this patent is extended or adjusted under 35 U.S.C. 154(b) by 717 days.

(21) Appl. No.: 10/894,638

(22) Filed: Jul. 20, 2004

(65) Prior Publication Data
US 2006/0020195 A1    Jan. 26, 2006

(51) Int. Cl.
*A61B 5/05* (2006.01)
(52) U.S. Cl. .................. 600/427; 382/128; 600/407
(58) Field of Classification Search ............ 600/407, 600/427; 382/128
See application file for complete search history.

(56) References Cited

U.S. PATENT DOCUMENTS

| | | | | |
|---|---|---|---|---|
| 3,082,322 | A | 3/1963 | Koerner et al. ............. 250/61.5 |
| 3,777,124 | A | 12/1973 | Pavkovich ................. 235/151 |
| 3,987,281 | A | 10/1976 | Hodes ..................... 235/151.3 |
| 3,991,310 | A | 11/1976 | Morrison ................... 250/312 |
| 4,882,741 | A | 11/1989 | Brown |
| 5,039,867 | A | 8/1991 | Nishihara et al. |
| 5,099,846 | A | 3/1992 | Hardy ..................... 128/653.1 |
| 5,107,839 | A | 4/1992 | Houdek et al. ............ 128/653.1 |
| 5,207,223 | A | 5/1993 | Adler ..................... 128/653.1 |
| 5,291,889 | A | 3/1994 | Kenet et al. .............. 128/653.1 |
| 5,301,674 | A | 4/1994 | Erikson et al. ........... 128/661.01 |
| 5,379,642 | A | 1/1995 | Reckwerdt et al. ............ 73/625 |
| 5,391,139 | A | 2/1995 | Edmundson .................. 600/7 |
| 5,411,026 | A | 5/1995 | Carol .................... 128/660.03 |
| 5,438,991 | A * | 8/1995 | Yu et al. ................... 600/426 |
| 5,442,675 | A | 8/1995 | Swerdloff et al. ............. 378/65 |
| 5,447,154 | A | 9/1995 | Cinquin et al. ........... 128/653.1 |
| 5,511,549 | A | 4/1996 | Legg et al. .............. 128/653.1 |
| 5,531,227 | A | 7/1996 | Schneider ................ 128/653.1 |
| 5,609,485 | A | 3/1997 | Bergman et al. ............ 434/262 |
| 5,673,300 | A | 9/1997 | Reckwerdt et al. ............ 378/65 |
| 5,690,108 | A | 11/1997 | Chakeres ................. 128/653.1 |
| 5,715,166 | A | 2/1998 | Besl et al. ................. 364/4.24 |
| 5,754,623 | A | 5/1998 | Seki |
| 5,778,043 | A | 7/1998 | Cosman |
| 5,810,007 | A | 9/1998 | Holupka et al. ........ 128/660.03 |

(Continued)

FOREIGN PATENT DOCUMENTS

EP    0 647 457 B1    1/2002

(Continued)

OTHER PUBLICATIONS

Written Opinion of the International Search Report for PCT/CA2005/001105 dated Oct. 27, 2005.

(Continued)

*Primary Examiner*—Long V Le
*Assistant Examiner*—Jacqueline Cheng
(74) *Attorney, Agent, or Firm*—Goodwin Procter LLP

(57) ABSTRACT

A patient's lesion is localized for the purpose of administering radiation treatment by obtaining a beam shape representation along one or more beam directions of a radiation treatment device. An image corresponding to the lesion is obtained from each beam direction, and the beam shape and image are fixed to a common coordinate system to facilitate alignment.

41 Claims, 10 Drawing Sheets

U.S. PATENT DOCUMENTS

| | | | |
|---|---|---|---|
| 5,991,703 A | 11/1999 | Kase | 702/167 |
| 6,019,724 A | 2/2000 | Gronninsaeter et al. | 600/439 |
| 6,106,470 A | 8/2000 | Geiser et al. | 600/443 |
| 6,117,081 A | 9/2000 | Jago et al. | 600/443 |
| 6,122,341 A | 9/2000 | Butler et al. | 378/20 |
| 6,129,670 A | 10/2000 | Burdette et al. | 600/427 |
| 6,269,143 B1 | 7/2001 | Tachibana | |
| 6,285,805 B1 | 9/2001 | Gueziec | 382/299 |
| 6,292,578 B1 | 9/2001 | Kalvin | 382/131 |
| 6,325,758 B1* | 12/2001 | Carol et al. | 600/439 |
| 6,345,114 B1 | 2/2002 | Mackie et al. | 382/132 |
| 6,359,959 B1 | 3/2002 | Butler et al. | 378/20 |
| 6,385,286 B1 | 5/2002 | Fitchard et al. | 378/65 |
| 6,390,982 B1 | 5/2002 | Bova et al. | 600/443 |
| 6,405,072 B1 | 6/2002 | Cosman | |
| 6,438,202 B1 | 8/2002 | Olivera et al. | 378/65 |
| 6,516,046 B1 | 2/2003 | Fröhlich et al. | 378/65 |
| 6,535,574 B1 | 3/2003 | Collins et al. | 378/65 |
| 6,546,073 B1 | 4/2003 | Lee | 378/65 |
| 6,553,152 B1 | 4/2003 | Miller et al. | 382/294 |
| 6,560,311 B1 | 5/2003 | Shepard et al. | 378/65 |
| 6,591,127 B1 | 7/2003 | McKinnon | 600/411 |
| 6,628,983 B1 | 9/2003 | Gagnon | 600/431 |
| 6,636,622 B2 | 10/2003 | Mackie et al. | 382/132 |
| 6,661,870 B2 | 12/2003 | Kapatoes et al. | 378/65 |
| 6,683,985 B1 | 1/2004 | Kase et al. | 382/203 |
| 2001/0035871 A1 | 11/2001 | Bieger et al. | 345/630 |
| 2002/0018588 A1 | 2/2002 | Kusch | 382/131 |
| 2002/0065461 A1* | 5/2002 | Cosman | 600/426 |
| 2002/0082494 A1 | 6/2002 | Balloni et al. | 600/410 |
| 2002/0156375 A1 | 10/2002 | Kessman et al. | 600/439 |
| 2002/0176541 A1 | 11/2002 | Schubert et al. | 378/205 |
| 2002/0183610 A1 | 12/2002 | Foley et al. | 600/407 |
| 2002/0188194 A1 | 12/2002 | Cosman | 600/426 |
| 2003/0018232 A1 | 1/2003 | Elliott et al. | 600/1 |
| 2003/0112922 A1* | 6/2003 | Burdette et al. | 378/65 |
| 2003/0153825 A1* | 8/2003 | Mooradian et al. | 600/407 |
| 2005/0251029 A1* | 11/2005 | Khamene et al. | 600/427 |

FOREIGN PATENT DOCUMENTS

| | | |
|---|---|---|
| WO | 99/27839 A2 | 6/1999 |
| WO | 99/27839 A3 | 6/1999 |
| WO | 03/076003 A2 | 9/2003 |
| WO | 03/076003 A3 | 9/2003 |

OTHER PUBLICATIONS

International Search Report for PCT/CA2005/001105 dated Oct. 27, 2005.

Besl et al., *A Method for Registration of 3d Shapes*, IEEE Transactions on Pattern Analysis and Machine Intelligence 14(2):239-256 (1992).

Booth, *Modelling the impact of treatment uncertainties in radiotherapy*, University of Adelaide, Mar. 2002), Section 2.4 (http://thesis.library.adelaide.edu.au/uploads/approved/adt-SUA20020816.175301/public/03chapter2.pdf.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. *Intraobserver and Interobserver Variability of MR Imaging- and CT-derived Prostate Volumes after Transperineal Interstitial Permanent Prostate Brachytherapy*, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al., *Three Dimensional Conformal External Beam Treatment of Prostate Cancer* http://prostate-help.org/download/pilgrim/10rad.pdf.

Hanks et al., *Clinical and Biochemical Evidence of Control of Prostate Cancer at 5 Years After External Beam Radiation*, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., *Development of a Semi-Automatic Alignment Tool for Accelerated Localization of the Prostate*, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing., pp. 196-213 (1992).

Krempien et al., *Daily patient set-up control in radiation therapy by coded light projection*, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) http://www.phoenix5.org/Infolink/Michalski/#3.

Paskalev et al., *Daily Target Localization for Prostate Patients based on 3-D Image Correlation*, Phys. Med.. Biol., vol. 49, pp. 931-939 (2004).

Pennec et al,. *A Framework for Uncertainty and Validation of 3-D Registration Methods Based on Points and Frames*, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., *Conventional vs. Conformal Radiotherapy for Prostate Cancer: Preliminary Results of Dosimetry and Acute Toxicity*, Int. J. Radiation Oncology Biol. Phys., 34(3):555-564.

Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-671 (2000).

Robinson, *Advances in Multi-Modal Data Analysis: The ANALYZE Software Environment*, http://www.ii.metu.edu.tr/~med-ii/makaleler/analyze_sw_enve.pdf, 5 pages. Downloaded on Aug. 10, 2004.

Soffen E.M. et al. *Conformal static field radiation therapy treatment of early prostate cancer versus non-conformal techniques: A reduction in acute morbidity*. Int J Radiat Oncol Biol Phys, 24: 485-488 (1992).

Thayananthan, A. et al., http://mi.eng.cam.ac.uk/~bdrs2/papers/thayananthan_cvpr03.pdf, pp. 1-8. Downloaded from the Internet on Aug. 10, 2004.

Tome et al., *Commissioning and Quality Assurance of an Optically Guided Three-dimensional Ultrasound Target Localization System for Radiotherapy*, Med. Phys., 29(8):1781-1788 (2002).

Zhang, *Iterative Point Matching for Registration of Free-Form Curves and Surfaces*, International Journal of Computer Vision, 13(2): 119-152 (1994).

http://www.ucsf.edu/jpouliot/Course/chapter5.htm.

http://www.acmp.org/meetings/hershey_2001/highlights/benedict.pdf.

http://www.ucsf.edu/jpouliot/Course/Lesson22.htm.

http://www.gemedicalsystems.com/patient/see_treat/positioning.html.

http://www.emoryradiationoncology.org/high-technology.htm.

http://www.varian.com/pinf/imr000c.html.

http://www.ucsf.edu/jpouliot/Course/conformal_radiation_therapy.htm.

Supplementary Partial European Search Report for EP Application No. 5763463, dated Nov. 30, 2009, 7 pages.

* cited by examiner

VERIFYING LESION CHARACTERISTICS USING BEAM SHAPES

TECHNICAL FIELD

This invention relates to methods and systems for verifying anatomical features of a patient undergoing radiation therapy and, more particularly, to methods and systems for positioning patients using planned radiation beam shapes.

BACKGROUND INFORMATION

Radiation-emitting devices are used for the treatment of cancerous tumors within patients. The primary goal of treating cancerous tumors with radiation therapy is the complete eradication of the cancerous cells, while the secondary goal is to avoid, to the maximum possible extent, damaging healthy tissue and organs in the vicinity of the tumor. Typically, a radiation therapy device includes a gantry that can be rotated around a horizontal axis of rotation during the delivery of a therapeutic treatment. A particle linear accelerator ("LINAC") is located within the gantry, and generates a high-energy radiation beam of therapy, such as an electron beam or photon (x-ray) beam. The patient is placed on a treatment table located at the isocenter of the gantry, and the radiation beam is directed towards the tumor or lesion to be treated.

Radiation therapy typically involves a planning stage and a treatment stage. In the planning stage, an X-ray computed tomography (CT) scanner (or similar device) is used to acquire images of a lesion. These images are used to accurately measure the location, size, contour, and number of lesions to be treated in order to establish an isocenter, a dose distribution, and various irradiation parameters in an attempt to irradiate the lesion while minimizing damage to surrounding healthy tissue.

The advent of 3D conformal radiation therapy (3DCRT) and intensity modulated radiation therapy (IMRT) has improved the ability to minimize this damage. 3DCRT and IMRT use multiple, intersecting, shaped radiation beams, each of which geometrically conforms to the shape of a tumor from the view point of the origin of the radiation beam (the "beam's eye view," or "BEV"). Various types of devices are used to conform the shape of the radiation treatment beam to encompass the tumor along the radiation treatment BEV as it traverses the patient's body into the tumor. One such beam-shielding device is the multi-leaf collimator ("MLC").

LINACs with MLCs facilitate delivery to a patient of radiation beams with arbitrary shapes and distributions. The MLC patterns can be defined during planning, and coupled with 3D conformal treatment planning techniques, they allow treatment plans to be more flexible and complex. Such MLC-based 3DCRT plans prescribe radiation field geometries tailored to fit the tumor's shape more accurately than previous, 2D block-shaped plans. As a result, higher doses can be targeted at the tumor, requiring tighter safety margins around the tumor to avoid damaging healthy tissue by exposing it to the higher, deadlier doses.

These capabilities have direct implications for radiotherapy treatment verification methods and, more specifically, on patient position verification because as radio-oncologists' dose irradiation volumes become smaller and more intricately sculpted to conform to the tumor, and the doses prescribed become higher, tumor position verification or tumor localization accuracy requirements become more critical. The result of misalignment, whether due to daily organ displacement (motion) and/or incorrect positioning of the patient on the treatment table, is that the conformal dose of radiation may not be delivered to the correct location within the patient's body. Because of the time constraints imposed during the treatment phase of the process, methods that provide fast, accurate, and reliable lesion alignment and displacement compensation data are of great benefit to a radiation technologist administering treatment.

SUMMARY OF THE INVENTION

The present invention provides systems and methods for localizing, verifying, and validating the position of a cancerous organ, lesion, or tumor (collectively referred to herein as a lesion) with respect to its intended treatment position prior to the delivery of radiation treatment, preferably using visual confirmation of the position of the organ or lesion with respect to the MLC port shape (as determined by the placement of the MLC leaves). In general, the invention relates to fixing one or more representations of beam shapes corresponding to a treatment device during a treatment planning session and a pre-treatment image of the lesion to be treated to a common coordinate system such that the two images can be aligned, and proper patient and/or organ positional adjustments can be made. The present invention facilitates rapid and accurate treatment position verification just prior to treatment delivery in a fraction of the time required by conventional methods.

In one aspect, a method for improved spatial localization of a patient's lesion for the purpose of administering radiation treatment includes obtaining a first beam shape representation (generated, for example, during a treatment planning session) with respect to the beam direction of the treatment device, obtaining an image corresponding to the lesion from the beam direction of the treatment device (during, for example, a treatment delivery session) and fixing the first beam shape and the image to a common coordinate system to facilitate alignment.

The treatment device can include one or more beam-shielding devices that affect the beam shape, such as the physical arrangement of the leaves within an MLC. In some embodiments, the leaves of the MLC can be adjusted manually, programmatically, or using a combination of manual and programmatic methods to conform the beam shape about the lesion. In some cases, the adjustments can be made during a treatment delivery session. The images corresponding to the tumor or lesion can be any of a three-dimensional ultrasound image, a CT image, an MRI image, or a PET image acquired after the planning stage for the purposes of administering radiation treatment. In some embodiments, the image corresponding to the lesion is a three-dimensional image, and may further be rendered as a set of surface elements. In some embodiments, the method can further include aligning the image with the beam shape such that the beam shape substantially encompasses the image of the lesion and subsequently adjusting the position of the patient to compensate for the alignment, adjusting the position of the patient in real time such that the beam shape substantially encompasses the lesion, or in some cases adjusting the leaves of the MLC such that the adjusted beam shape encompasses the lesion. In some embodiments, both the beam shape and the patient position can be adjusted such that the beam shape encompasses the lesion.

In some embodiments where the image of the lesion is a three-dimensional image, the method may further include obtaining additional beam shape representations from different directions, and fixing each of the beam shape representations and the three-dimensional image to the common coordinate system. In such embodiments, the beam shape representations can comprise an MLC intersection volume, thus allowing the three-dimensional image and the MLC intersection volume to be aligned. The patient position can then be adjusted according to the alignment. The common coordinate system can be established using a laser system in, for example, a treatment room.

In another aspect, a method for positioning a patient for the administration of radiation treatment of a lesion includes providing a treatment device that emits at least one beam having a beam shape; generating a three-dimensional ultrasound image of the lesion; fixing the beam shape and the ultrasound image to a treatment coordinate system; superimposing the beam shape and the ultrasound image based on the treatment coordinate system, and adjusting the position of the patient such that the ultrasound image is substantially encompassed by the beam shape.

In another aspect, a system for positioning a patient for the administration of radiation treatment of a lesion includes a register for establishing one or more beam shape representations taken from one or more perspectives of a treatment device; a processor for determining an alignment of the beam shape representations with an image corresponding to the lesion using a common coordinate reference system (established, for example, using a laser system arranged in a treatment room) such that the image is substantially encompassed by the beam shape representations; and a controller for controlling a patient support device in accordance with the alignment.

In some embodiments, the treatment device can include one or more beam-shielding devices that affect the beam shape, such as the physical arrangement of the leaves within an MLC. In some embodiments, the leaves of the MLC can be adjusted manually, programmatically, or using a combination of manual and programmatic methods to conform the beam shape about the lesion. In some embodiments, the beam shape representations can comprise an intersection volume. The images corresponding to the lesion can be any of a three-dimensional ultrasound image, a CT image, an MRI image, or a PET image acquired after the planning stage for the purposes of administering radiation treatment. In embodiments where the image is a three-dimensional image, the processor can further segment the image into a set of surface elements. In some embodiments, the controller can adjust the position of the patient support device such that the beam shape substantially encompasses the lesion, or in some embodiments, align the image and the beam shape representations, and subsequently adjust the position of the patient accordingly.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

In the past, radiation therapy plans were reviewed in a single plane as a two-dimensional cross-section of the lesion to be treated and the distribution of radiation outside (i.e., above and below or in front of and behind) the plane was assumed to be adequate. This assumption is valid if there are no significant changes in the shape or contour of an organ or tumor outside of the single plane. However, such radiation-therapy techniques do not account for the variability of the human anatomy. Three-dimensional conformal radiation therapy (3DCRT) allows a three-dimensional and volumetric appreciation of a target volume and surrounding normal tissues that are not dependent on arbitrary and regular geometric shapes. The goal of 3DCRT is to have the prescribed radiation dose distribution be shaped like or "conform to" a target volume to the greatest extent possible without exposing healthy tissue to potentially harmful doses of radiation.

A 3DCRT device used in conjunction with the present invention generally includes a beam-shielding device within the treatment head of a treatment device, a control unit within a housing connected to a treatment processing unit, and a gantry which can be rotated about an axis in the course of a therapeutic treatment. The treatment head is fixed to the gantry for movement around the treatment table, and includes a linear accelerator for generating high powered radiation such as electron, photon, or other detectable types of radiation suitable for the treatment of patients. During treatment, the radiation beam is focused at a structure, tumor, or lesion within a patient at the intersection of the radiation beam axes (the "isocenter"). The rotatable gantry allows for different beam angles and radiation distributions without having to move the patient.

Figure 1:
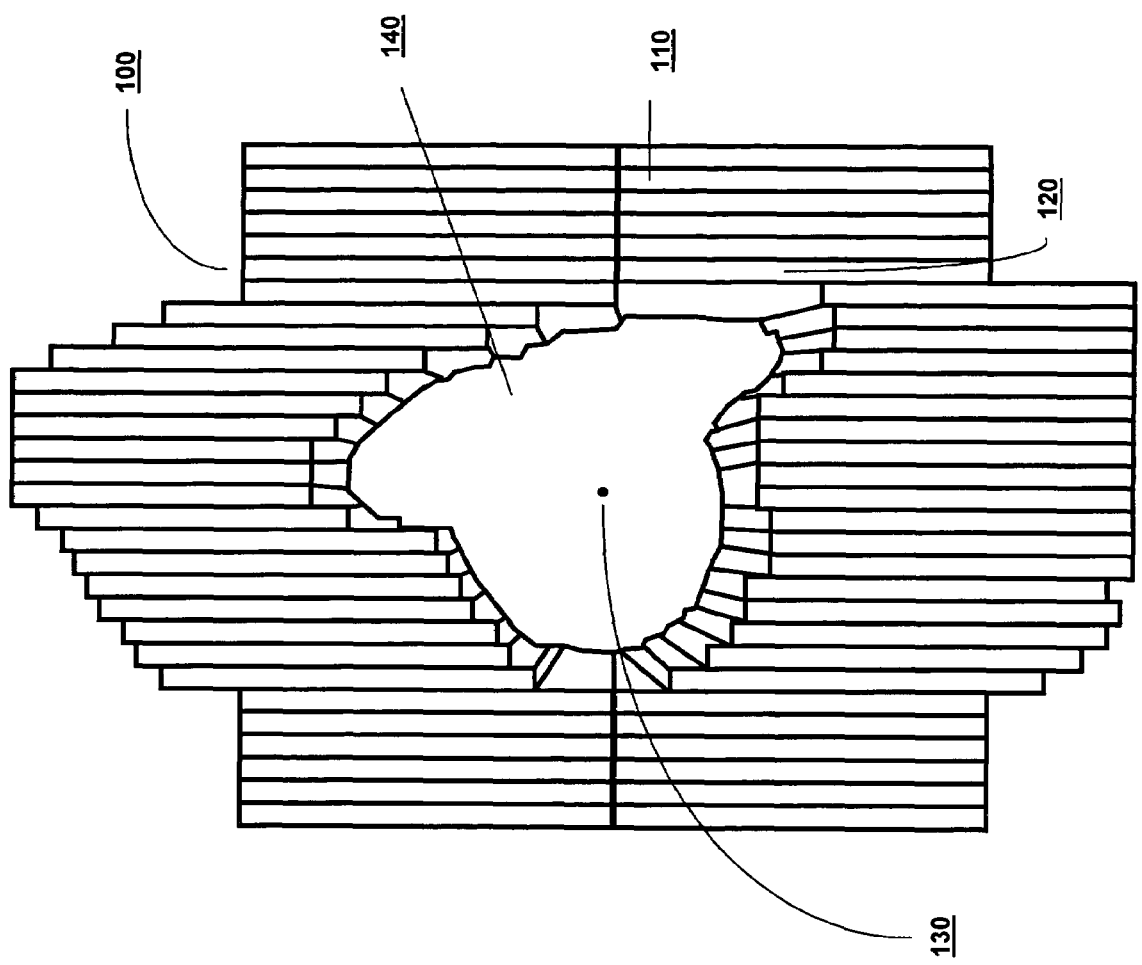
FIG. 1 is an elevation of an MLC used in an embodiment of the invention.
Figure 2:
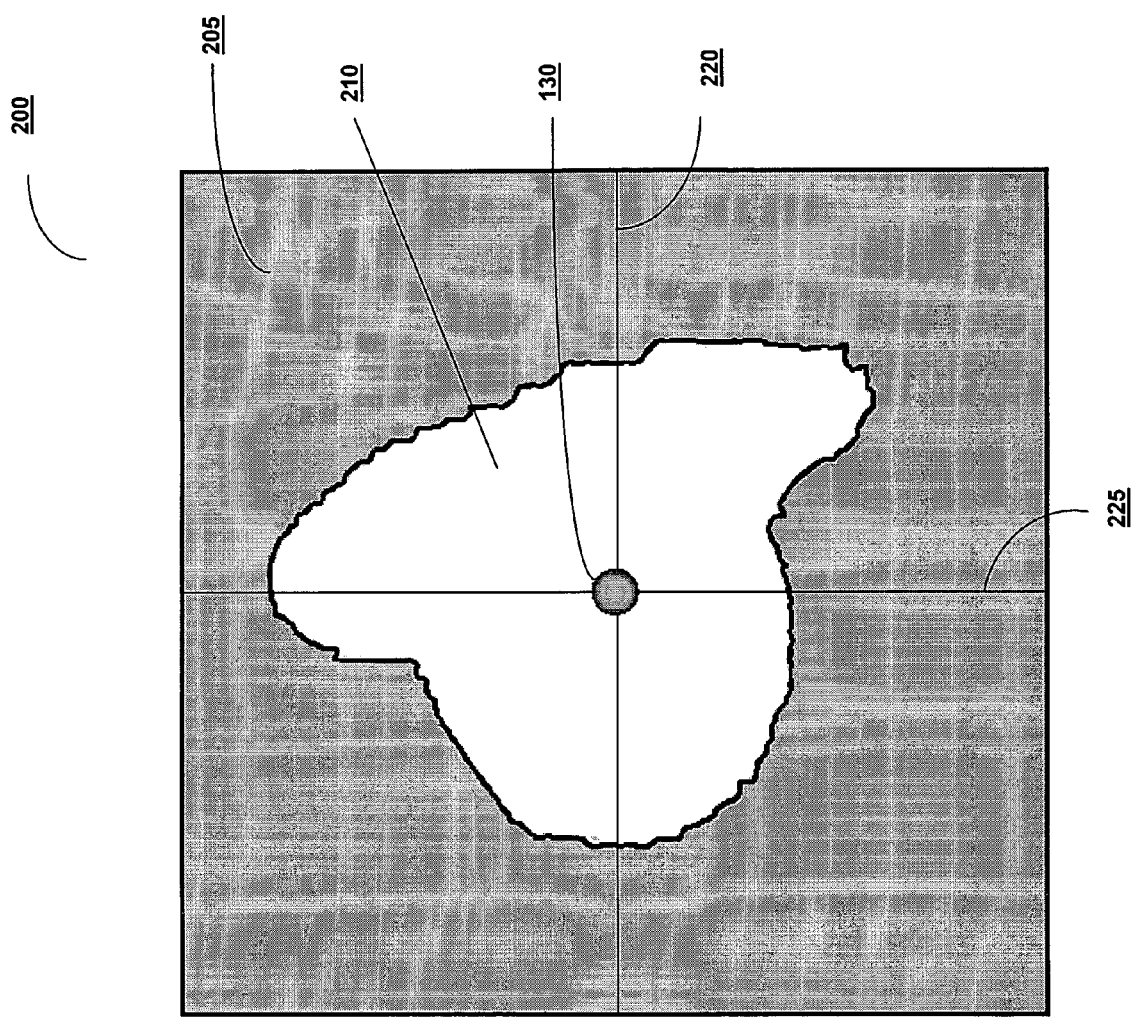
FIG. 2 schematically illustrates a beam shape generated by the MLC of FIG. 1.
Figure 3:
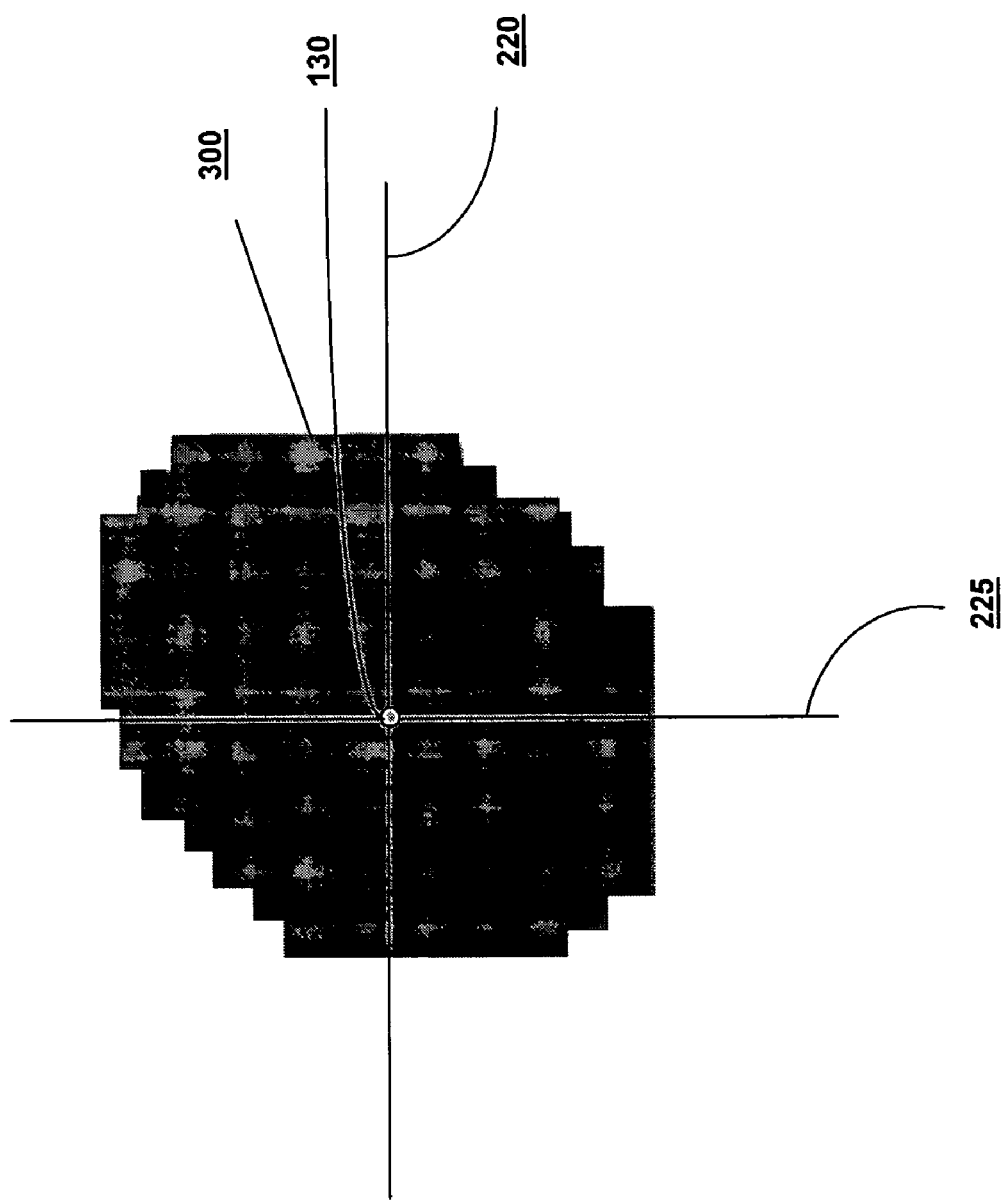
FIG. 3 is a simplified representation of a different beam shape generated by the MLC of FIG. 1.

Referring to FIG. 1, a beam-shielding device 100 is provided in the path of each beam to define a radiation field. One example of a beam-shielding device 100 is a multi-leaf collimator ("MLC") that includes a plurality of opposing plates or leaves 110, 120 mounted between the radiation source and patient. The leaves 110, 120 can vary in width, length, or thickness, and are substantially impervious to the emitted radiation. Adjusting the leaves 110, 120 blocks the radiation according to the leaf pattern, thus shielding healthy tissue from the radiation being applied to the tumor. The leaves 110, 120 are movable in a direction generally perpendicular to the beam as to allow for changes in the size and shape of an irradiation field 140. This permits an essentially arbitrary shaped beam that can better conform to the size and shape of the lesion, tumor, or structure being treated. Within the thus-shaped beam, the energy of the beam is typically uniform. FIG. 2 illustrates the resulting sectional representation 200 of the radiation field, including a shielded area 205 and an outline of the unshielded area 210. Also denoted is the x-axis 220 and y-axis 225 of the MLC, which converge at the treatment isocenter 130 of the field. The axes 220, 225 define a common coordinate reference system for use in registering the beam shape with other images, and coincide with the laser coordinate system found in the treatment room, which also intersect at the treatment isocenter 130. During the treatment planning stage, beam shapes are generally generated as the maximum projected shape of the target at isocenter 130 for the given beam direction. FIG. 3 illustrates one possible representation of a coarse representation of a resulting beam shape 300 simplified for illustrative purposes.

Figure 4:
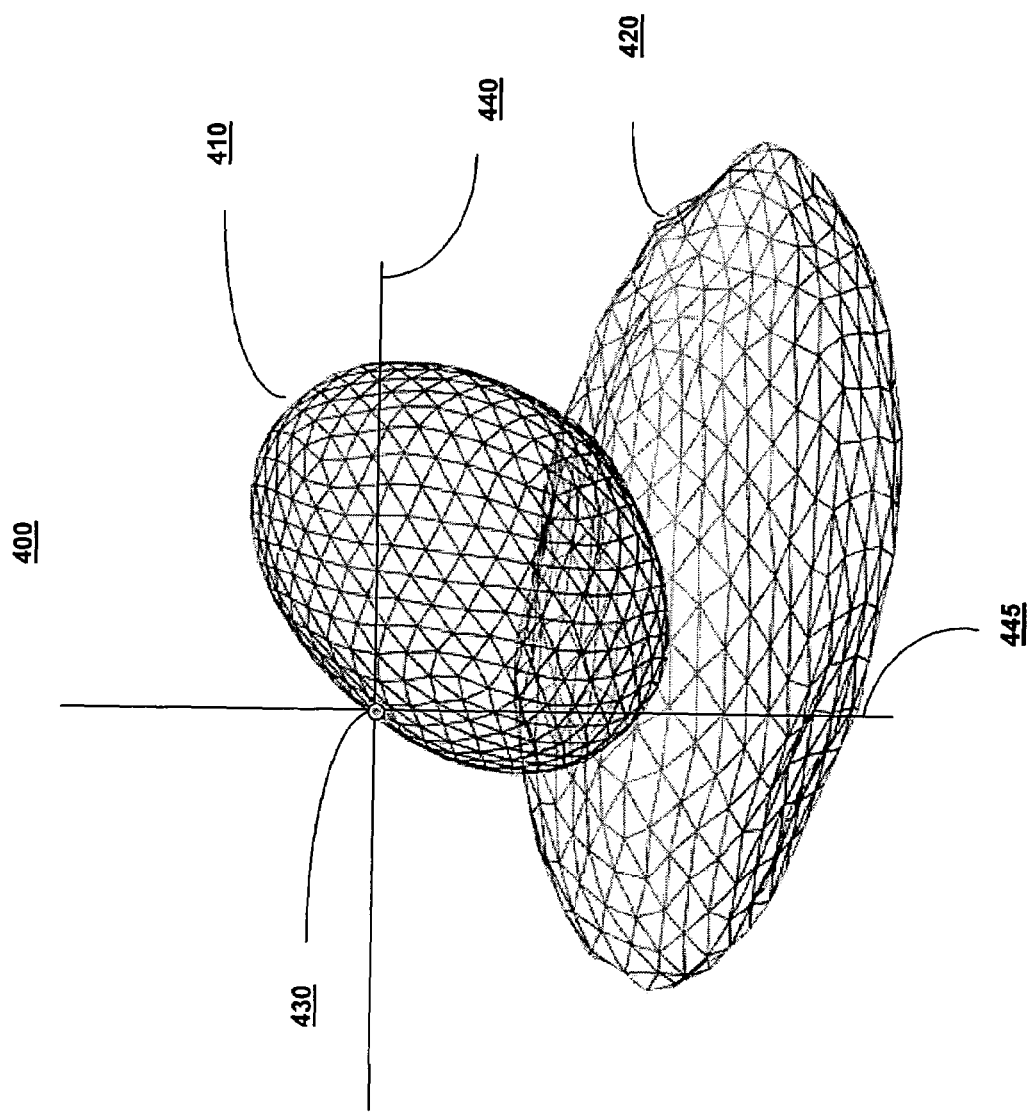
FIG. 4 schematically illustrates anatomical features of a patient.

Given the close proximity of the tumor to healthy surrounding structures, and the physician's choice of radiation beam directions, the beam shape 300 may encompass portions of healthy surrounding structures. FIG. 4 illustrates a composite image 400 characterizing the target structure 410 and a nearby normal structure 420. The target structure can be any anatomical feature such as a cancerous organ, tumor, or lesion such as a lymph node in the neck region, a cancerous prostate, or a tumor bed in a breast. In some embodiments, the target structure 410 can also represent a non-cancerous organ to be used as a landmark for positioning the patient during treatment planning and/or treatment delivery. In some cases, the target structure 410 is located proximate to a critical normal structure 420 such as the bladder, the rectum, the spinal cord, or other healthy tissue. The goal of conformal therapy is to deliver the appropriate amount of prescribed radiation to the target structure 410 while minimizing the exposure of the normal structure 420. The target structure 410 and the normal structure 420 images are acquired relative to a treatment coordinate system defined by the treatment isocenter 430 and the x-axis 440, y-axis 445, and z-axis (not shown) lasers which intersect at the treatment isocenter 430.

In some embodiments, the images characterizing the target structure are obtained just prior to treatment to observe the most current size, shape, and placement of the target structure 410 and any surrounding tissue or organs. The images of the target structure 410 and normal structure 420 can be represented in two or three dimensions, and generated using one or more of numerous techniques known in the art such as three-dimensional ultrasound imaging, CT scanning, magnetic resonance imaging, or PET scanning. The scanning devices are referenced to the treatment coordinate system defined by the treatment isocenter 430, and the treatment coordinate axes 440 and 445 so as to obtain images of the anatomical structures of interest using the treatment coordinate system. For example, where the structures 410, 420 represent a cancerous lesion in the prostate and a healthy bladder respectively, the images can be semi-automatically segmented and/or mapped from 3D ultrasound scans of the pelvis using image segmentation and/or contour mapping methods known in the art. Furthermore, the structures 410, 420 can be manually contoured or segmented from CT scans, MRI scans, or PET/CT scans acquired at treatment time with the patient in the treatment position using similar techniques.

Figure 5:
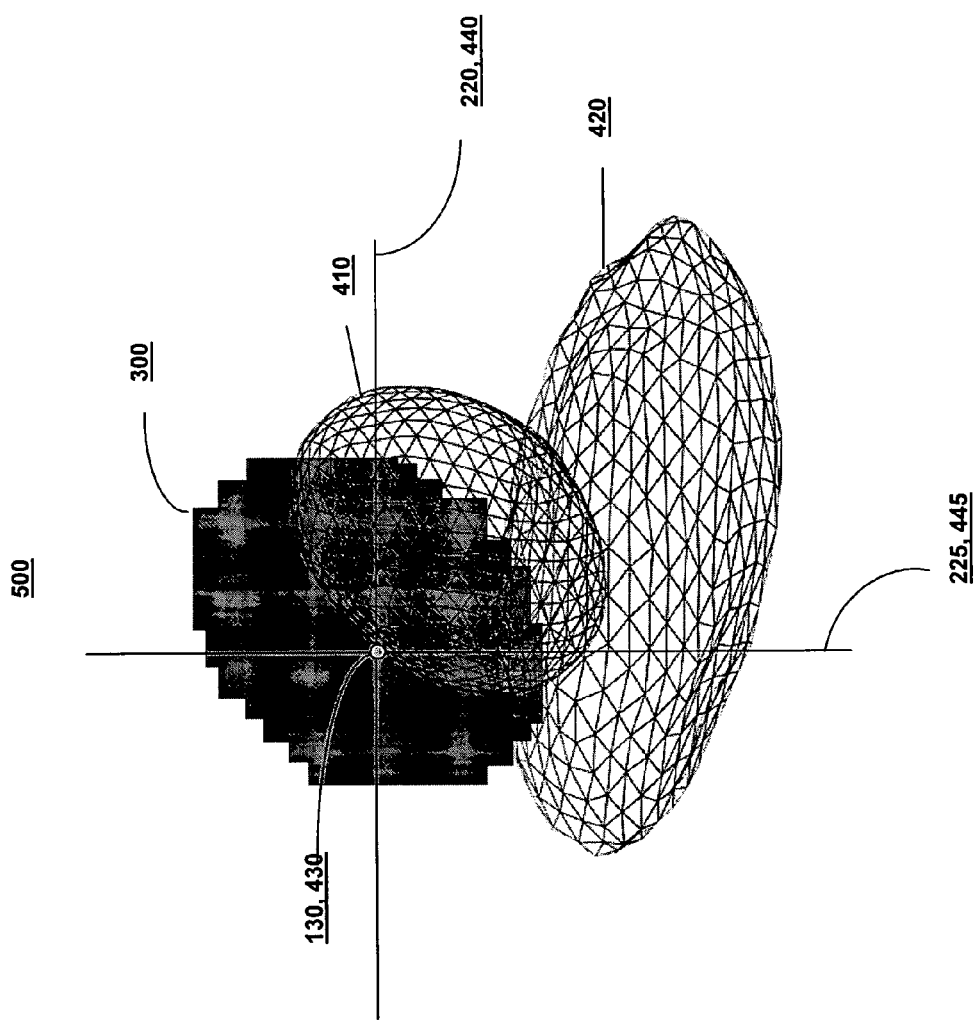
FIG. 5 illustrates the beam shape of FIG. 3 against the anatomical features shown in FIG. 4.
Figure 6:
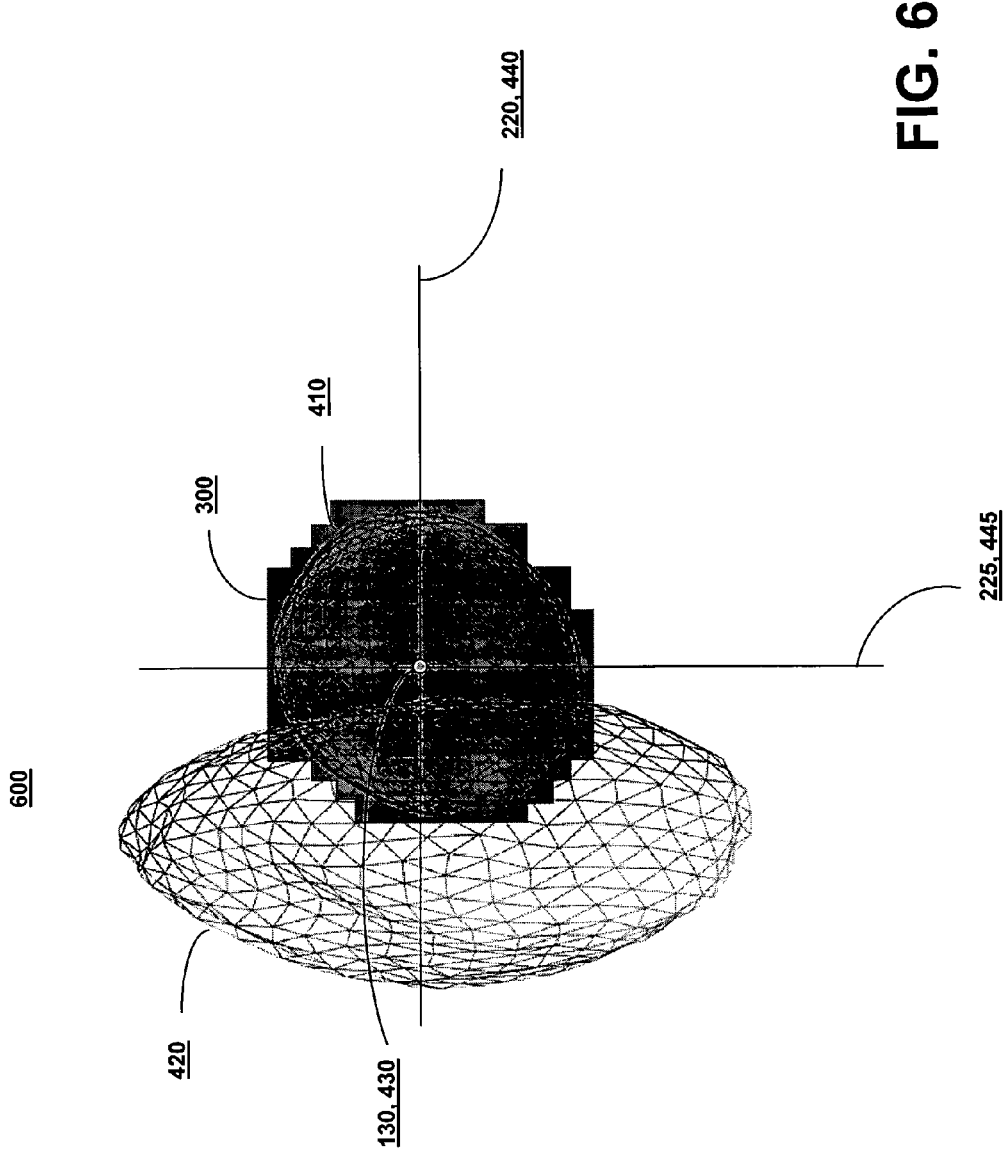
FIG. 6 illustrates the beam shape of FIG. 3 fully surrounding one of the anatomical features shown in FIG. 4.

Referring to FIGS. 5 and 6, the beam shape 300 generated during the treatment planning session is registered with the images corresponding to the target structure 410 and normal structure 420 generated during the treatment session and in anticipation of treatment radiation delivery, by aligning the MLC treatment coordinate system defined by 130, 220, and 225 and the image treatment coordinate system defined by 430, 440, and 445, respectively, to create composite images 500 and 600. In some embodiments, the beam shape 300 can be manipulated and selectively superimposed onto the images of the target structure 410 and normal structure 420. In this example, the composite image 500 indicates that the beam shape 300 designed during treatment planning is misaligned with the target structure 410. In some instances, the misalignment of the beam shape 300 and the target structure 410 can be a result of improper patient positioning or movement of the target structure, and thus repositioning of the patient is called for. In other cases, the misalignment can be caused by changes in the physical characteristics of the target structures 410, such as growth or morphism. In some cases, both are present. As a result of these changes during the period between treatment planning and treatment delivery, the originally planned beam shape 300 and/or the current patient positioning is not optimal. Through adjustments to patient positioning, the position of the lesion 410 with respect to the treatment coordinate system and treatment isocenter of the MLC can be adjusted such that the lesion 410 is aligned with the beam shape 300. Through real-time adjustments to the leaves of the MLC at treatment time, the beam shape 300 can be modified to address any physical changes of the target structure 410 or surrounding normal structures 420. FIG. 6 illustrates the beam shape 300 and the target structure 410 post-alignment, where the beam shape 300 fully encompasses the lesion 410. In some instances, the optimal alignment may be such that the beam shape 300 does not fully encompass the target structure 410 due to nearby organs that cannot withstand the radiation treatment, or complex shaping of the structure 410.

Figure 7:
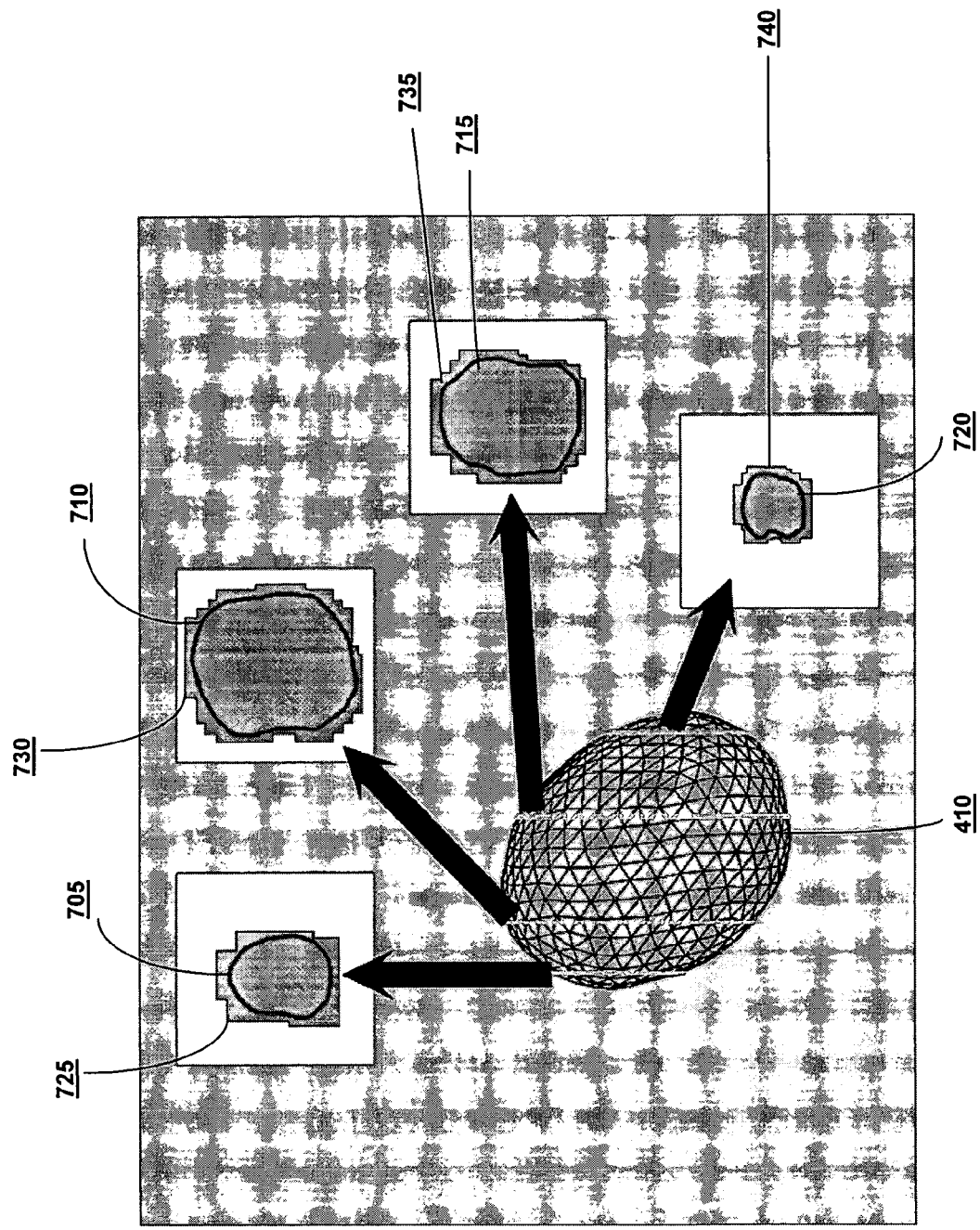
FIG. 7 shows a series of cross-sections of an anatomical feature taken along the section lines shown.

During the treatment planning stage, beam shapes are generated representing the maximum projected shapes of the target at isocenter 130 for each planned beam direction. The intersection of the beam shapes from the multiple beam directions generates an MLC intersection volume. FIG. 7 is a volumetric representation of the corrected alignment of FIG. 6 showing the MLC volume encompassing the 3D tumor image. Arbitrary cross-sectional planar reconstructions of the MLC volume and the 3D tumor image can be obtained to further aid in patient localization and alignment. Referring to FIG. 7, four planar-reconstruction cross-sectional images, 705, 710, 715, and 720 of the target structure 410 represent different cross-sectional outlines of the target structure 410 along arbitrarily selected planes through the reconstructed 3D tumor image. For each of these cross-sectional images, the corresponding planar-reconstruction cross-sectional images of the MLC volume are also shown, 725, 730, 735, and 740. The MLC volume encompasses all (or in some cases substantially all) of the target structure 410 at that particular cross-section of the target structure 410. This results in four distinct beam shapes 725, 730, 735, and 740, each associated with one arbitrary cross-section of the target structure 410. The four beam shapes can then be used to verify more comprehensively size, shape, and location of the target structure 410 just prior to treatment using the methods and systems described herein.

Figure 8:
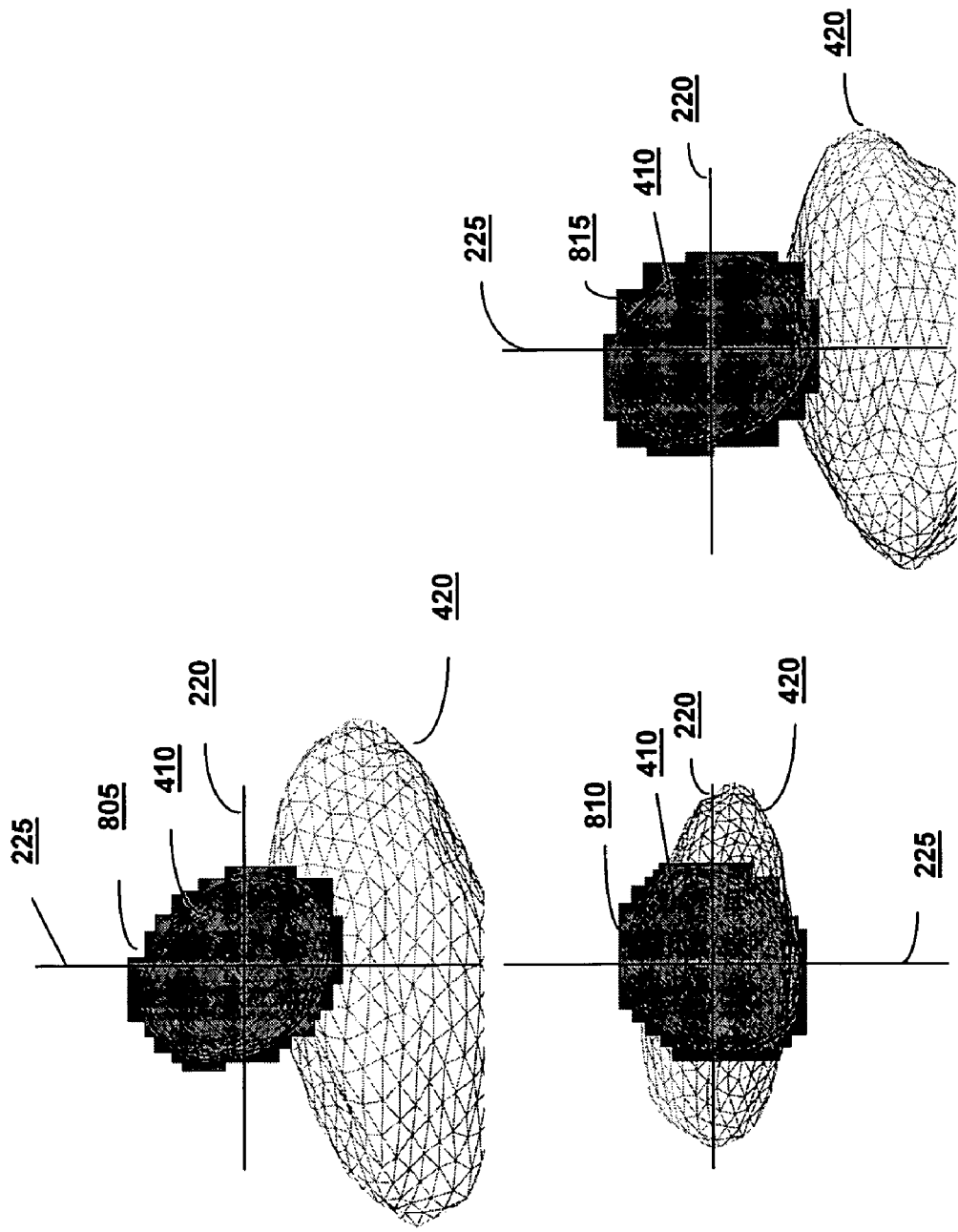
FIGS. 8A-8C illustrate the manner in which a single anatomical structure, varying in profile, is surrounded by a beam shape from each of multiple beam perspectives.

Beam shapes can be obtained from different beam directions, thus providing additional opportunities to conform (on a beam-by-beam basis) the treatment plan to the shape of the target structure 410 and allowing for more accurate positioning of the patient prior to treatment. FIG. 8 illustrates three views of the target structure 410 and the normal, healthy structure 420, registered with three different beam shapes

805, 810, and 815, and the associated coordinate system axes 220, 225, each taken from a different beam direction, or "beam's eye view" through the leaves of the associated MLC. During the treatment planning phase, a radiation oncologist or other radiation treatment planning specialist determines an optimal beam shape 805 for the lesion 410 from a first direction, as described above. After determining a first appropriate beam shape 805, the gantry is rotated, within the treatment planning simulation software, changing the beam direction such that the radiation addresses the target structure 410 from a different angle. The process of adjusting the leaves is repeated, and a second beam shape 810 is determined for the second treatment angle. This can be repeated any number of times, until the physician or other dosimetry specialist is satisfied that the treatment plan is appropriate and that the prescribed dose can be delivered to the target with as much sparing of health surrounding structures. In some embodiments, the multiple beam shapes may be combined into a three-dimensional volume that represents the intersection of all beams the desired radiation field from multiple beam directions, whereas in some embodiments the appropriate alignment for each beam shape is determined on a beam-by-beam bases, and the results are then used in conjunction with each other to adjust the patient position.

The treatment plan designed during the treatment planning session is then used to deliver the radiation during one or more treatment delivery sessions. Generally, treatment delivery occurs within a few days or weeks of the preparation of the treatment plan, and can include one or more sessions, depending on the type of lesion being treated, the patient's overall health, as well as other factors. As described above, the lesion being treated and surrounding tissue and organs can undergo morphological changes and move between the planning stage and treatment delivery, as well as between each treatment session. In some instances, the treatment delivery sessions can occur over a period of weeks or even months, giving rise to further uncertainties in patient positioning and physiology. To compensate for these changes, the multiple beam shapes 805, 810, and 815 or more generally, arbitrary multi-planar reconstruction beam shapes 725, 730, 735, and 740 can be used to validate location and to adjust the patient position within three dimensional space. Prior to a radiation treatment session, the technician obtains updated images, such as three-dimensional ultrasound images, of the target structure 410 and surrounding tissue that characterizes the most current position and shape of the structure, which are then superimposed with the previously obtained intersection volume derived from the multiple beam shapes 805, 810, and 815. The updated images are then aligned to the coordinate system of the intersection volume, in the case where the beam shapes are combined into a volume, or on sequentially on a beam-by-beam basis. This may be done through simple correlation means, or conventional fitting and interpolation algorithms known to those in the art. Updated images can be obtained prior to the first treatment session and all subsequent sessions, or some subset of the treatment sessions, depending on the amount of time between sessions, the anatomy of the patient, as well as other factors. In some embodiments, the beam shapes from multiple beam directions can be modified in order to encompass the lesion without having to move the patient or the patient support device.

Once the updated images and the intersection volume have been registered, the technician can determine the proper adjustments to make such that the target structure 410 is substantially encompassed within the target volume. The adjustments can be made by manually simulating movement of the target structure 410 using a device such as a pointer, a computer mouse, or other such input device and translating the simulated movements into absolute changes in patient positioning either through movement of a patient support device such as a treatment table, movement of the patient with respect to the treatment table, or both. In some embodiments, the adjustments can be made programmatically using software, e.g., using image-manipulation programs that find the best fit of a beam profile over a target structure. In other embodiments where real-time images of the target structure 410 are available, the technician can progressively adjust the patient or patient support device directly while viewing the results of the adjustments on a computer monitor until the desired position is achieved.

Figure 9:
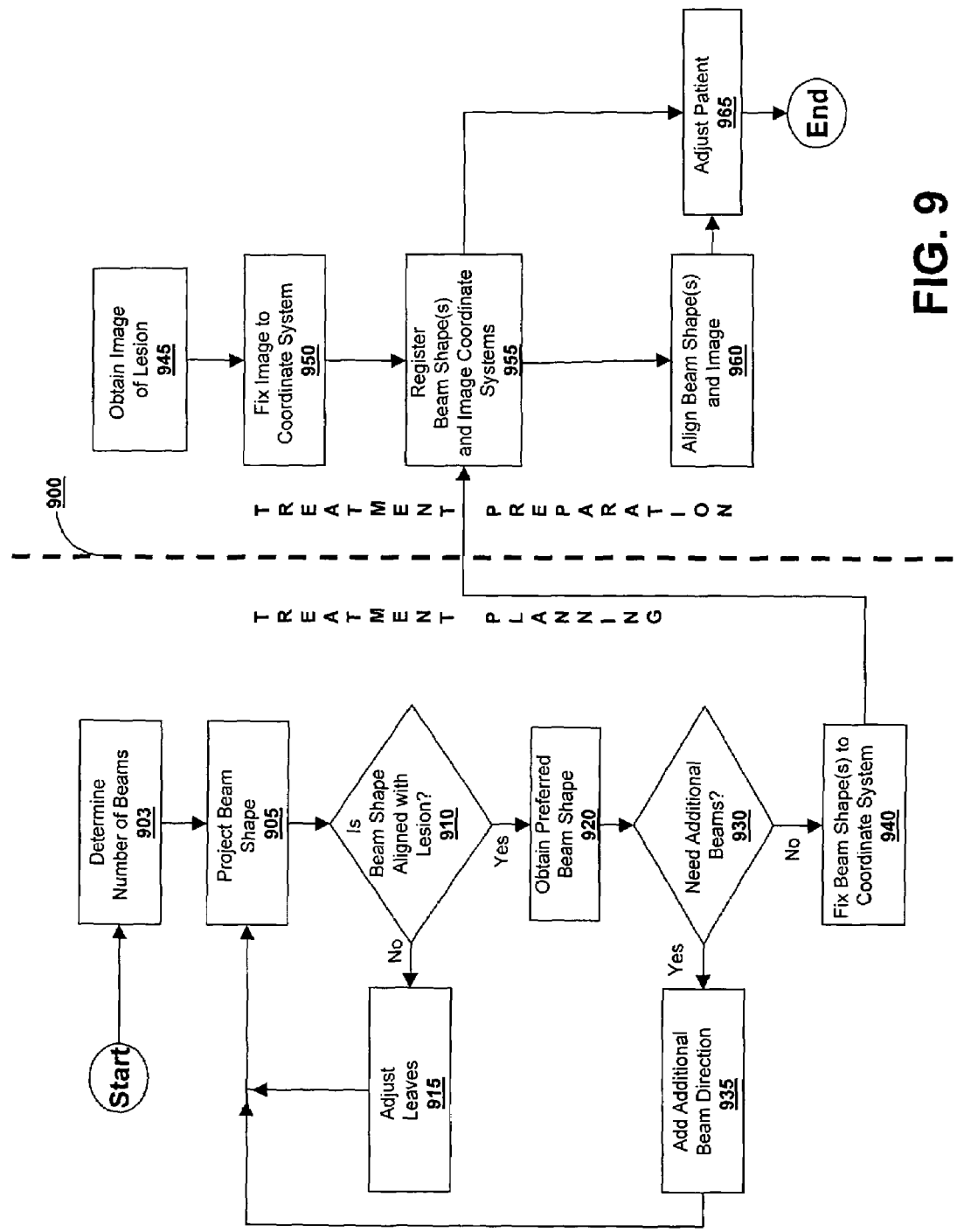
FIG. 9 is a flow diagram illustrating various embodiments of localization, alignment, and adjustment according to an embodiment of the invention.

FIG. 9 illustrates various embodiments of a method of localization and the resulting alignment and adjustment to improve the delivery of radiation treatment to a patient. As described above, the process is typically divided into two phases: a treatment planning phase (identified as the elements to the left of the dashed line 900), during which an oncologist or similarly trained physician prepares a treatment plan for the administration of radiation to a cancerous lesion; and a treatment preparation phase (identified as the elements to the right of the dashed line 900) during which a radiology technician positions the patient on the treatment table, makes any adjustments to the positioning based on lesion morphing or shifting, and administers the radiation according to the treatment plan. The treatment planning phase can occur substantially before the treatment preparation phase, or in some cases immediately preceding the treatment preparation phase, and may take place in the same room, or in some cases different rooms. As the time span increases between the phases, the target lesion has a greater opportunity to grow, morph, and change its positioning with respect to surrounding normal tissue and healthy organs, thus resulting in a need for positional compensation.

As an initial step, an oncologist or other specialist trained in dosimetry planning, such as a physicist or dosimetrist, determines the number of beams (step 903) necessary to deliver the appropriate radiation to the target lesion and to avoid subjecting healthy tissue to harmful levels. The beam shape is the maximum projected (step 905) shape at the isocenter of the target lesion from a particular beam direction. A determination is then made (step 910) as to whether the beam shape accurately reflects the shape and size of the lesion. If the beam shape is not accurate, the leaves are adjusted (step 915) and the beam shape is re-projected (step 905) and again compared to the lesion. In some instances, the adjustments to the leaves can be made manually by physically moving one or more leaves in a lateral direction perpendicular to the radiation beam. In other cases, the operator indicates the desired changes to the beam shape using a data input device such as a touch screen, a pointing device, or a keyboard, and the leaves are adjusted programmatically (or the adjustments are simulated) according to the instructions from the operator. Once the beam shape encompasses the lesion, it is captured (step 920) as an image, such as the beam shape 300 illustrated in FIG. 3.

In most instances, patients are treated with multiple beams since increasing the number of beams used will usually decrease the dose given to regions outside the intersecting beams. In such cases, the accuracy of the patient positioning can be further verified by aligning multiple beam shapes taken from separate directions with the image of the lesion for the corresponding beam directions. In such cases, the user determines if the number of beams stipulated by the physician in step 903 have been captured (step 930). If additional beams are needed, the beam direction is adjusted (step 935), and the process repeats: projecting the beam shape for each beam direction (step 905), determining if it is properly shaped (step 910), and potentially adjusting the leaves (step 915) to obtain the preferred beam shape (step 920). Once a sufficient number of beam shapes have been obtained, they can be combined into a beam shape intersection volume describing the radiation treatment plan as a three-dimensional model of the radiation field to be delivered to the patient, or used sequentially to determine a beam-by-beam alignment. Because the beam shapes are generated using the MLC device, the beam shapes can be aligned with the coordinate system of the MLC (step 940) which is equivalent to the treatment coordinate system. One example of a preferred alignment places the intersection of the axes at the treatment isocenter of the MLC radiation field, as illustrated in FIG. 2.

During the treatment preparation phase, one or more images characterizing the lesion (and in some cases, other surrounding structures) is generated (step 945) using one or more of the imaging modalities described above. Such images are taken in anticipation of the delivery of the radiation treatment to confirm lesion and/or organ location and identify any changes to the lesion. Images of the lesion are taken relative to the treatment coordinate system (step 950). The beam shape (in the case of a two-dimensional image) or the beam intersection volume (in the case of a three-dimensional image) is then registered with, or superimposed on the image by registering their common reference coordinate system (step 955).

By representing both the MLC beam shape and the image of the target lesion in a common reference coordinate system, the image can be manipulated such that the target lesion is substantially encompassed in the beam shape (step 960). The process of aligning the characterization of the target lesion to the beam shape involves moving the lesion with respect to the x-axis and/or the y-axis and/or z-axis of the coordinate system using any of a variety of image manipulation techniques. An example of output from the alignment step is a set of displacements (e.g., −4 pixels in the x direction, +8 pixels in the y direction and +12 pixels in the z direction) that describe the movement from the original position of the target structure to the position in which it is encompassed by the beam shape. These displacements can then be translated into a set of displacements for a patient support device, such as a treatment table of the LINAC, or the patient, just prior to treatment delivery. For example, a displacement of (−4, +8, +12) may translate into moving the treatment table 4 millimeters to the left, 8 millimeters up, and 12 millimeters in with respect to the gantry.

Alternatively, a technician may use real-time or virtual simulation techniques to bypass the alignment step and directly manipulate the patient or patient support device (step 965) while viewing the beam shape and a real-time image of the structure on a screen or monitor. In one embodiment, a technician can adjust the treatment table position with respect to the MLC until the image of the target structure is encompassed in the beam shape by manipulating an input device such as a joystick, keypad, or other input device and the use of beam's-eye-view or room-view displays. In another embodiment, the technician manually adjusts the position of the patient on a stationary treatment table until the desired position is reached. In some cases, the technician may employ a combination of both programmatic adjustments based on predetermined alignment displacements, and manual patient positioning techniques.

In other embodiments, the technician may alter the shape of the MLC port by adjusting the leaves just prior to treatment in lieu of moving the patient to correct displacement of the lesion, or for changes in the shape of the target lesion (due to swelling or other morphology), which may not be addressable by rotation or translation. For example, the target lesion can grow such that changing the MLC beam shape from each beam direction is the preferred method of treating the lesion in its entirety.

Figure 10:
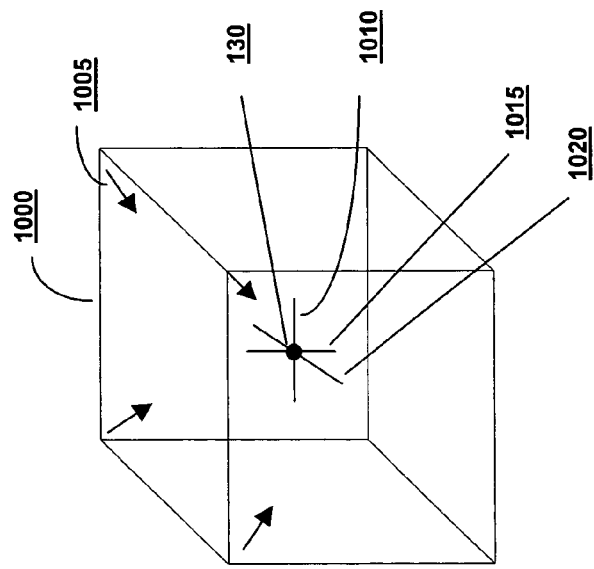
FIG. 10 schematically illustrates a room in which the methods and systems of an embodiment of the invention can be used.

FIG. 10 illustrates one example of how a laser sight system placed within a room is used to create the common coordinate system. The room 1000 can be used for treatment planning, treatment delivery, or both. In either case, a series of lasers 1005 are placed about the walls and/or ceiling of the room 1000 such that every position in space within the room 1000 can be expressed as a distance from the intersection of the laser beams 1005 along a set of axes 1010, 1015, 1020. With MLC (not shown) placed in the same room, the lasers can be aimed such that the intersection point of the beams corresponds to the isocenter 130 of the MLC, and the axes of the laser sight system and the MLC can be aligned.

Figure 11:
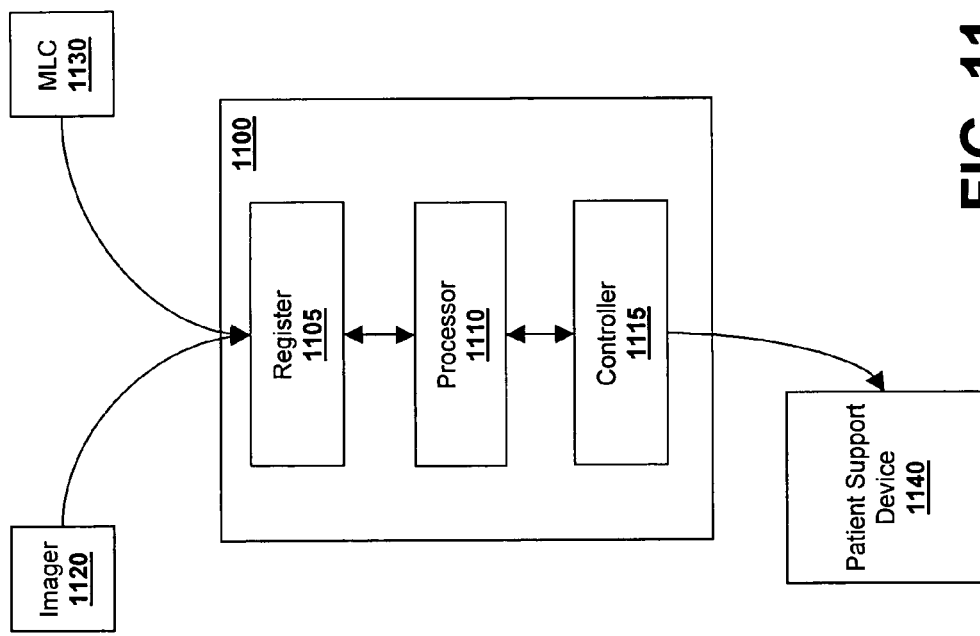
FIG. 11 is a schematic illustration of various embodiments of a system adapted to practice the methods of the present invention.

FIG. 11 schematically represents a hardware embodiment of the invention realized as a system 1100 for positioning a patient for the administration of radiation therapy. The system 1100 comprises a register 1105, a data processing device 1110, and a controller 1115.

The register, which may be any known organized data storage facility (e.g., partitions in RAM, etc.) 1105 receives images from an imager 1120 such as an MRI, CT/PET scanner, or ultrasound device. In some embodiments, the images can be stored on a data storage device separate from the imager (e.g., a database, microfiche, etc.) and sent to the system 1100. The register also receives a beam shape image from an MLC 1130. The beam shape can be a single image, and therefore a two-dimensional representation of the beam shape, or multiple images, which can be combined to comprise a three-dimensional intersection MLC volume. The register may receive the images and beam shapes through conventional data ports and may also include circuitry for receiving analog image data, and analog-to-digital conversion circuitry for digitizing the image data.

The register then provides the image and the beam shape(s) to the processor 1110 which registers the image and the beam shape(s) into one image using the common reference treatment coordinate system from the medical imaging device 1120 or the MLC 1130. The processor 1110 then either programmatically, or in response to instructions from the user of the system 1100, determines the proper alignment of the beam shape and the image such that the target lesion is substantially encompassed in the beam shape, or, in the case of multiple beam shapes defining an intersection volume, such that the lesion is substantially encompassed by the intersection volume from multiple beam directions. The processor calculates a set of displacements based on the movements needed for proper alignment of the image and beam shapes, which in turn are communicated to the controller 1115. The controller translates displacements into instructions representing physical movements of a patient support device 1140 and sends the instructions to the device 1140 in order to adjust the position of the patient in accordance with the alignment calculations. In some embodiments, the processor 1110 may also find the best fit of a beam shape to the lesion and suggest MLC variations to minimize radiation that is outside the lesion, to create treatment margins as described above, or as otherwise needed.

In some embodiments, the register 1105, processor 1110, and controller 1115 may implement the functionality of the present invention in hardware or software, or a combination of both on a general-purpose computer. In addition, such a program may set aside portions of a computer's random access memory to provide control logic that affects one or more of the image manipulation, fusion, alignment, and support device control. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for improved spatial localization of a patient's lesion for the purpose of administering radiation treatment, the method comprising the steps of:
   (a) obtaining a plurality of beam shape representations, each along a direction of a corresponding beam of a treatment device;
   (b) constructing a three-dimensional intersection volume from the plurality of beam shape representations;
   (c) obtaining a plurality of images corresponding to the lesion from each of the directions of the beams of the treatment device;
   (d) constructing a three-dimensional lesion image from the plurality of images;
   (e) fixing the three-dimensional intersection volume and the three-dimensional tumor image to a common coordinate system in order to facilitate volumetric alignment therebetween;
   (f) constructing a three-dimensional image comprising the three-dimensional lesion image and the three-dimensional intersection volume based on the common coordinate system; and
   (g) obtaining a plurality of cross-sectional reconstructions of the three-dimensional image, each cross-sectional reconstruction comprising a two-dimensional representation of the lesion and of the intersection volume.

2. The method of claim 1 wherein the treatment device includes one or more beam-shielding devices that affect the beam shape.

3. The method of claim 2 wherein the beam-shielding device is a MLC.

4. The method of claim 3 wherein the beam shape representations are based, at least in part, on the physical arrangement of leaves in the MLC.

5. The method of claim 4 wherein the beam shape representations are adjusted by adjusting the positions of the leaves within the MLC.

6. The method of claim 5 further comprising adjusting leaves within the MLC in order to conform beam shapes about the lesion.

7. The method of claim 6 wherein the leaves are adjusted manually.

8. The method of claim 6 wherein the leaves are adjusted programmatically.

9. The method of claim 6 wherein the adjustment is made during a treatment planning session.

10. The method of claim 1 wherein the plurality of images comprises images selected from the group of a three-dimensional ultrasound image, a CT image, an MRI image, and a PET image acquired after planning for purposes of treatment.

11. The method of claim 1 wherein the beam shapes are generated during a treatment planning session.

12. The method of claim 1 wherein the coordinate system is established using a laser system arranged within a treatment delivery room.

13. The method of claim 1 wherein the images are fixed to the coordinate system during a treatment delivery session.

14. A method for positioning a patient for the administration of radiation treatment of a lesion, the method comprising the steps of:
   (a) providing a treatment device emitting at least one beam, each beam having a beam shape;
   (b) generating a three-dimensional ultrasound image of the lesion;
   (c) generating a three-dimensional intersection volume from a plurality of beam shapes generated by the treatment device;
   (d) fixing the three-dimensional intersection volume to a treatment coordinate system;
   (e) fixing the ultra-sound image to the treatment coordinate system;
   (f) superimposing three-dimensional intersection volume and the three-dimensional ultrasound image based, at least in part, on the treatment coordinate system;
   (g) obtaining a plurality of cross-sectional reconstructions of the superimposed three-dimensional intersection volume and three-dimensional ultrasound image, each cross-sectional reconstruction comprising a two-dimensional representation of the lesion and of the intersection volume; and
   (h) adjusting the position of the patient such that the three-dimensional ultrasound image is substantially volumetrically encompassed by the three-dimensional intersection volume.

15. The method of claim 14 wherein the treatment device includes, for each beam, at least one beam-shielding device that affects the shape of the beam shape.

16. The method of claim 15 wherein the beam-shielding device is a MLC.

17. The method of claim 16 wherein each beam shape is based, at least in part, on the physical arrangement of leaves in the MLC as determined during a treatment planning session.

18. The method of claim 17 further comprising for each beam, adjusting leaves within the MLC in order to conform the beam shape about the lesion.

19. The method of claim 18 wherein the leaves are adjusted manually.

20. The method of claim 18 wherein the leaves are adjusted programmatically.

21. The method of claim 14 further comprising rendering the three-dimensional ultrasound image of the lesion as a set of surface elements.

22. The method of claim 14 further comprising adjusting the position of the patient so that each two-dimensional representation of the lesion is substantially encompassed in its corresponding two-dimensional representation of the intersection volume.

23. A system for positioning a patient for the administration of radiation treatment of a lesion, the system comprising:
(a) a register configured to establish a plurality of beam shape representations, each taken from one or more perspectives of a treatment device;
(b) a processor configured to generate a three-dimensional intersection volume from the plurality of beam shape representations, and determining an alignment of the three-dimensional intersection volume and a three-dimensional image corresponding to the lesion using a common coordinate reference system such that the three-dimensional image corresponding to the lesion is substantially volumetrically encompassed by the three-dimensional intersection volume, and obtain a plurality of cross-sectional reconstructions of the superimposed three-dimensional intersection volume and three-dimensional image, each cross-sectional reconstruction comprising a two-dimensional representation of the lesion and of the intersection volume; and
(c) a controller configured to control a patient support device in accordance with the alignment.

24. The system of claim 23 wherein the treatment device includes one or more beam-shielding devices that affect the beam shape.

25. The system of claim 24 wherein the beam-shielding device is a MLC.

26. The system of claim 25 wherein the plurality of beam shape representations are based, at least in part, on the physical arrangement of leaves in the MLC as determined during a treatment planning session.

27. The system of claim 26 wherein the plurality of beam shape representations are adjusted by adjusting the positions of the leaves within the MLC.

28. The system of claim 27 wherein the leaves are adjusted manually.

29. The system of claim 27 wherein the leaves are adjusted programmatically.

30. The system of claim 27 wherein the adjustments are made during a treatment planning session.

31. The system of claim 23 wherein the three dimensional image is constructed from one or more images selected from the group of a two-dimensional ultrasound image, a three-dimensional ultrasound image, a CT image, an MRI image, and a PET image acquired after planning for purposes of treatment.

32. The system of claim 23 wherein the image corresponding to the lesion is a three-dimensional image and the processor segments the image into a set of surface elements.

33. The system of claim 23 further comprising a laser system arranged within a treatment delivery room for establishing the common coordinate reference system.

34. The system of claim 23 the processor is further configured to adjust the position of the patient so that each two-dimensional representation of the lesion is substantially encompassed in its corresponding two-dimensional representation of the intersection volume.

35. A system for improved spatial validation of the position of a patient's lesion for the purpose of administering radiation treatment, comprising:
(a) a MLC configured to obtain a plurality of beam shape representations, each along a direction of a corresponding beam of a treatment device;
(b) a register configured to construct a three-dimensional intersection volume from the plurality of beam shape representations;
(c) an imager configured to obtain a plurality of images corresponding to a patient's lesion from each of the directions of the beams of the treatment device;
(d) a processor configured to:
(i) construct a three-dimensional lesion image from the plurality of images;
(ii) fix the three-dimensional intersection volume and three-dimensional lesion image to a common coordinate system in order to facilitate volumetric alignment therebetween and;
(iii) obtaining a plurality of cross-sectional reconstructions of the superimposed three-dimensional intersection volume and three-dimensional image, each cross-sectional reconstruction comprising a two-dimensional representation of the lesion and of the intersection volume.

36. The system of claim 35 wherein the processor is further configured to adjust one or more shielding devices within the treatment device in order to conform the beam shape representations about the lesion.

37. The system of claim 36 wherein the beams are adjusted manually.

38. The system of claim 36 wherein the beams are adjusted programmatically.

39. The system of claim 35 wherein the processor is further configured to segment the image corresponding to a patient's lesion into a set of surface elements.

40. The system of claim 35 further comprising a patient support device configured to adjust the position of the patient so that the three-dimensional intersection volume substantially encompasses the three-dimensional lesion image.

41. The system of claim 35 wherein the processor is further configured to align the three-dimensional lesion image with the three-dimensional intersection volume so that the three-dimensional lesion image is substantially encompassed within the three-dimensional intersection volume.

* * * * *